(12) United States Patent
Shimizu

(10) Patent No.: US 9,782,108 B2
(45) Date of Patent: Oct. 10, 2017

(54) BED-LEAVING SENSOR AND BED-LEAVING DETECTION METHOD

(71) Applicant: SUMITOMO RIKO COMPANY LIMITED, Komaki-shi, Aichi (JP)

(72) Inventor: Atsuki Shimizu, Komaki (JP)

(73) Assignee: SUMITOMO RIKO COMPANY LIMITED, Komaki (JP)

( * ) Notice: Subject to any disclaimer, the term of this patent is extended or adjusted under 35 U.S.C. 154(b) by 106 days.

(21) Appl. No.: 14/862,651

(22) Filed: Sep. 23, 2015

(65) Prior Publication Data
US 2016/0007886 A1    Jan. 14, 2016

Related U.S. Application Data

(63) Continuation of application No. PCT/JP2014/063883, filed on May 26, 2014.

(30) Foreign Application Priority Data

Jun. 28, 2013 (JP) ................................. 2013-136944

(51) Int. Cl.
*G08B 21/22* (2006.01)
*A61B 5/11* (2006.01)
(Continued)

(52) U.S. Cl.
CPC ........ *A61B 5/1115* (2013.01); *G08B 21/0461* (2013.01); *G08B 21/22* (2013.01);
(Continued)

(58) Field of Classification Search
CPC ..... A61B 5/1115; A61B 5/1117; G08B 21/22; G08B 23/00; G08B 29/185; G01L 1/205
(Continued)

(56) References Cited

U.S. PATENT DOCUMENTS 7,656,299 B2 * 2/2010 Gentry .................. A61B 5/1113
340/562
2006/0028350 A1 * 2/2006 Bhai ..................... A61B 5/1115
340/666
(Continued)

FOREIGN PATENT DOCUMENTS

JP    2007-190269 A    8/2007
JP    2007-313189 A    12/2007
(Continued)

OTHER PUBLICATIONS

Jan. 7, 2016 International Preliminary Report on Patentability issued in International Patent Application No. PCT/JP2014/063883.
(Continued)

*Primary Examiner* — Hung T Nguyen
(74) *Attorney, Agent, or Firm* — Oliff PLC

(57) ABSTRACT

A bed-leaving sensor for detecting bed-leaving by a user on a bed, including: a sitting position detection member that detects a sitting position of the user based on a detection value of a pressure sensor arranged on the bed; a foot movement detection member for detecting foot movement of the user based on the detection value of the pressure sensor; and a bed-leaving behavior detection member that detects bed-leaving behavior of the user with the sitting position or the foot movement being detected within a preset bed-leaving expectation region as a condition.

8 Claims, 6 Drawing Sheets

(51) Int. Cl.
*G08B 21/04* (2006.01)
*G08B 29/18* (2006.01)
*A61B 5/103* (2006.01)

(52) U.S. Cl.
CPC .......... *G08B 29/185* (2013.01); *A61B 5/1036* (2013.01); *A61B 2562/0247* (2013.01); *A61G 2203/34* (2013.01)

(58) Field of Classification Search
USPC ...... 340/573.4, 573.5, 665, 666; 5/600, 618; 177/45, 144
See application file for complete search history.

(56) References Cited

U.S. PATENT DOCUMENTS

2009/0260158 A1* 10/2009 Kazuno ................ A61B 5/1115
5/600

2013/0146371 A1* 6/2013 Shih ..................... G01G 19/445
177/144

FOREIGN PATENT DOCUMENTS

| JP | 2007-330336 A | 12/2007 |
| JP | 2009-039453 A | 2/2009 |
| JP | 2012-011174 A | 1/2012 |
| JP | 2012-029871 A | 2/2012 |
| JP | 2013-031770 A | 2/2013 |

OTHER PUBLICATIONS

Jul. 1, 2014 International Search Report issued in International Patent Application No. PCT/JP2014/063883.

Sep. 20, 2016 Office Action issued in Japanese Patent Application No. 2013-136944.

* cited by examiner

BED-LEAVING SENSOR AND BED-LEAVING DETECTION METHOD

INCORPORATED BY REFERENCE

The disclosure of Japanese Patent Application No. 2013-136944 filed on Jun. 28, 2013, including the specification, drawings and abstract is incorporated herein by reference in its entirety. This is a Continuation of International Application No. PCT/JP2014/063883 filed on May 26, 2014.

BACKGROUND OF THE INVENTION

1. Field of the Invention

The present invention relates to a bed-leaving sensor that detects bed-leaving by a user on a bed, and a bed-leaving detection method.

2. Description of the Related Art

For example, in a hospital, nursing facility or the like, when a care receiver such as a physically disabled patient, an elderly person or the like who is in bed tries to get out from the bed by himself, there is a risk of tumbling or falling down. In light of that, examination has been done of aiding a care receiver with leaving the bed by using a bed-leaving sensor for detecting bed-leaving when the care receiver leaves the bed, and when it is detected by the bed-leaving sensor that the care receiver is leaving the bed, a caregiver is notified.

As this kind of bed-leaving sensor, in Japanese Unexamined Patent Publication No. JP-A-2012-29871, proposed is a bed-leaving sensor for which a pressure sensor is arranged on a bed, and when the body pressure of the user detected by the pressure sensor is a designated value or less, it determines that the person left the bed. Also, in Japanese Unexamined Patent Publication No. JP-A-2012-11174, proposed is a bed-leaving sensor for which a load sensor is provided at each leg part, and when the movement volume of the load center of gravity detected by those load sensors goes to a designated value or less, it determines that the person left the bed. However, with the bed-leaving sensors noted in JP-A-2012-29871 and JP-A-2012-11174, bed-leaving is detected after the user has completely left the bed, so the detection timing is slow, and there is the risk of an accident such as the person having fallen down or the like already having occurred when the caregiver rushed to check.

Meanwhile, in Japanese Unexamined Patent Publication No. JP-A-2007-313189, proposed is a movement discrimination device for detecting that the user has sat up based on the movement volume and movement direction of the user's body center of gravity. However, with the movement discrimination device noted in JP-A-2007-313189, since it is determined a person has left the bed only by the user sitting up, there is a high risk of false alarms, with bed-leaving detected even when it is simply sitting up unrelated to leaving the bed, and in addition to there being a high risk of false alarms, the detection timing is early, and there is a risk of the caregiver being called frequently.

SUMMARY OF THE INVENTION

The present invention has been developed in view of the above-described matters as the background, and it is an object of the present invention to provide a bed-leaving sensor with a novel structure and a bed-leaving detection method that is able to detect a user leaving the bed before bed-leaving is completed, and with good accuracy.

The above and/or optional objects of this invention may be attained according to at least one of the following aspects of the invention. The following aspects and/or elements employed in each aspect of the invention may be adopted at any possible optional combinations.

A first aspect of the present invention provides a bed-leaving sensor for detecting bed-leaving by a user on a bed, comprising: a sitting position detection member that detects a sitting position of the user based on a detection value of a pressure sensor arranged on the bed; a foot movement detection member for detecting foot movement of the user based on the detection value of the pressure sensor; and a bed-leaving behavior detection member that detects bed-leaving behavior of the user with the sitting position or the foot movement being detected within a preset bed-leaving expectation region as a condition.

With the bed-leaving sensor according to the present invention, it is possible to detect bed-leaving when the sitting position of the user is detected within a preset bed-leaving expectation region. Bed-leaving with the present invention includes bed-leaving behavior connected to bed-leaving. Also, the bed-leaving expectation region means a region on a bed for which it is assumed the buttocks of the user will be placed when the user is leaving the bed, and for example, it means an outer peripheral part of the bed, or, when a railing for preventing falling out of the bed is provided, it means the foot side area for which the railing is not provided. Also, with the present invention, bed-leaving is determined at the point that the user trying to leave the bed has taken a sitting position posture in a designated bed-leaving expectation region, and it is possible to detect bed-leaving before the user completely leaves the bed. In addition to that, since simply a sitting position does not mean bed-leaving is determined, it is possible to detect bed-leaving behavior with better precision, and it is possible to reduce the risk of false alarms. Furthermore, bed-leaving is also determined when movement of the feet within the bed-leaving expectation region is detected. By doing this, it is possible to determine bed-leaving at the point in time when a user trying to leave the bed moves his feet within the bed-leaving expectation region in order to step off from the bed. As a result, it is possible to detect bed-leaving more promptly. In this way, with the bed-leaving sensor of the present invention, it is possible to detect the bed-leaving behavior of a user on a bed trying to leave the bed, so it is possible to detect bed-leaving before the user completely leaves the bed, and to detect bed-leaving with good precision.

A second aspect of the present invention provides the bed-leaving sensor according to the first aspect, wherein the bed-leaving expectation region is set to be a foot side region on the bed.

With this aspect, by setting the bed-leaving expectation region for detecting the sitting position of the user and movement of the feet to be a foot side region of the bed at which the user's feet are positioned in a normal use state, it is possible to detect the sitting position of the user and movement of the feet of the user trying to leave the bed with good precision.

A third aspect of the present invention provides the bed-leaving sensor according to the first or second aspect, wherein the pressure sensor is arranged only at a bed-leaving possibility region on the bed.

The bed-leaving possibility region on the bed with this aspect is the region on the bed for which the user can get down from the bed, and means the region for which the outer circumference is open with the bed without being blocked by a railing, wall or the like. Also, with this aspect, it is possible to make the pressure sensor compact, and to ensure good sleep comfort for the user.

A fourth aspect of the present invention provides the bed-leaving sensor according to any one of the first through third aspects, wherein the sitting position detection member sets a determination area in a periphery of a pressure sensing center of a region in which pressure of a given contact threshold value or greater is detected within a preset sitting position determination region on the pressure sensor, and the sitting position is detected based on a ratio of a total pressure detected within the determination area occupying a total pressure detected within the sitting position determination region, a breadth of the region in which the pressure of the contact threshold value or greater is detected within the sitting position determination region, and the total pressure detected within the sitting position determination region.

With this aspect, by using the breadth of the region detected by the pressure sensor and the size of the pressure, it is possible to detect with good precision that the user is in the sitting position. Specifically, the size of the region for which pressure of the contact threshold value or greater is detected correlates to the buttocks, and by determining a person is in the sitting position when the size of the pressure is a size correlating to when pressure is focused on the buttocks by the sitting position, it is possible to distinguish between lying on one's back, lying on one's side, and the sitting position. The pressure sensing center can also be an item for which the center part of the region in which the pressure is detected can be roughly identified. For example, the pressure sensing center can be the center of gravity of the region for which the pressure is detected, or can be the area center of the region for which the pressure is detected.

A fifth aspect of the present invention the bed-leaving sensor according to the fourth aspect, wherein the pressure sensing center is a center of gravity of the region in which the pressure of the contact threshold value or greater is detected with the pressure sensor.

With this aspect, by using the center of gravity as the pressure sensing center, it is possible to identify the center part of the region for which an output value of the contact threshold value or greater is detected with good precision, and possible to increase the determination precision of the sitting position.

A sixth aspect of the present invention provides the bed-leaving sensor according to the fourth aspect, wherein the pressure sensing center is an area center of the region in which the pressure of the contact threshold value or greater is detected with the pressure sensor.

With this aspect, by using the area center as the pressure sensing center, it is possible to simplify the pressure sensing center calculation process, and it is possible to more quickly determine the sitting position.

A seventh aspect of the present invention provides the bed-leaving sensor according to any one of the first through sixth aspects, wherein the foot movement detection member detects the foot movement based on a breadth of a region in which pressure of a given contact threshold value or greater has been detected within a preset foot pressure detection region on the pressure sensor, a total pressure detected within the foot pressure detection region across a given time, and a maximum pressure value detected within the foot pressure detection region.

With this aspect, by using as conditions the breadth of the region for which pressure is detected, the maximum value of the pressure, and the continuous detection of pressure of the designated value or greater across a designated time, it is possible to detect the movement of the feet at the time an attempt is made to leave the bed with better precision. Specifically, when an attempt is made to leave the bed, by the user putting a load on the feet on the bed, a larger pressure is applied than when turning over in bed or the like. Then, by using as a condition the continuous detection of pressure of a designated value or greater across a designated time, it is possible to detect with good precision the movement of the feet when trying to leave the bed that is different from turning over in bed or the like.

An eighth aspect of the present invention provides the bed-leaving sensor according to any one of the first through seventh aspects, further comprising a notification member for notifying that the bed-leaving behavior of the user has been detected.

With this aspect, with the notification member, when the user on the bed is trying to leave the bed, it is possible to notify a caregiver or the like, for example. As the notification member, for example, it is possible to have a sound ring, to notify with a sound or warning light at a nurse station separated from the room in which the bed is equipped, or the like.

A first aspect of the present invention provides a bed-leaving detection method for detecting bed-leaving by a user on a bed, comprising: a sitting position detection step for detecting a sitting position of the user based on a detection value of a pressure sensor arranged on the bed; a foot movement detection step for detecting foot movement of the user based on the detection value of the pressure sensor; and a bed-leaving behavior detection step for detecting bed-leaving behavior of the user with the sitting position or the foot movement being detected within a preset bed-leaving expectation region as a condition.

With the bed-leaving detection method according to the present invention, the same as with the bed-leaving sensor of the present invention described above, it is possible to detect bed-leaving behavior of a user trying to leave the bed with good precision before the user on the bed leaves the bed.

A second aspect of the present invention provides the bed-leaving detection method according to the first aspect, wherein a foot side region on the bed is set as the bed-leaving expectation region.

With this aspect, by setting the bed-leaving expectation region at which the sitting position and the foot movement of the user is detected to the foot side region of the bed at which the feet of the user are positioned in a state of normal use, it is possible to detect the sitting position of the user and the foot movement of the user attempting to leave the bed with good precision.

A third aspect of the present invention provides the bed-leaving detection method according to the first or second aspect, wherein with the sitting position detection step, a determination area is set in a periphery of a pressure sensing center of a region in which pressure of a given contact threshold value or greater is detected within a preset sitting position determination region on the pressure sensor, and the sitting position is detected based on a ratio of a total pressure detected within the determination area occupying a total pressure detected within the sitting position determination region, a breadth of the region in which the pressure of the contact threshold value or greater is detected within the sitting position determination region, and the total pressure detected within the sitting position determination region. With this aspect, the same as with the bed-leaving sensor of the present invention described above, it is possible to detect the sitting position of the user with good precision.

A fourth aspect of the present invention provides the bed-leaving detection method according to any one of the first through third aspects, wherein the foot movement detection step detects the foot movement based on a breadth of a region in which pressure of a given contact threshold value or greater is detected within a preset foot pressure detection region on the pressure sensor, a total pressure detected within the foot pressure detection region across a given time, and a maximum pressure value detected within the foot pressure detection region. With this aspect, the same as with the bed-leaving sensor of the present invention described above, it is possible to detect with better precision the movement of the feet when an attempt is made to leave the bed.

With the bed-leaving sensor and the bed-leaving detection method according to the present invention, the determination of bed-leaving was set with detection of the sitting position or the foot movement within a designated bed-leaving expectation region as a condition. By doing this, it is possible to detect leaving of the bed with good precision before the person trying to leave the bed completely leaves the bed.

BRIEF DESCRIPTION OF THE DRAWINGS

The foregoing and/or other objects, features and advantages of the invention will become more apparent from the following description of a preferred embodiment with reference to the accompanying drawings in which like reference numerals designate like elements and wherein.

DETAILED DESCRIPTION OF PREFERRED EMBODIMENTS

Figure 1:
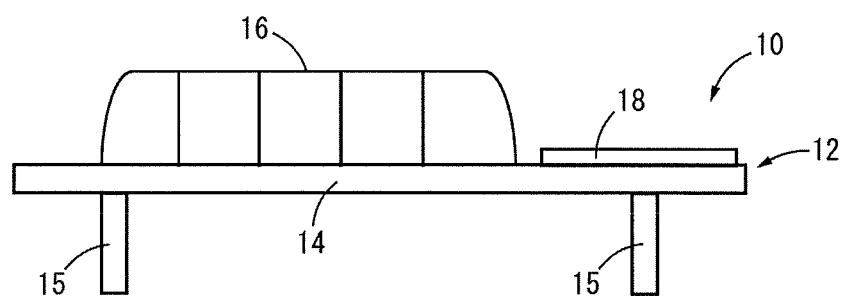
FIG. 1 is a side view of a bed equipped with a bed-leaving sensor of a first embodiment of the present invention.

Following, we will describe embodiments of the present invention while referring to the drawings.

Figure 2:
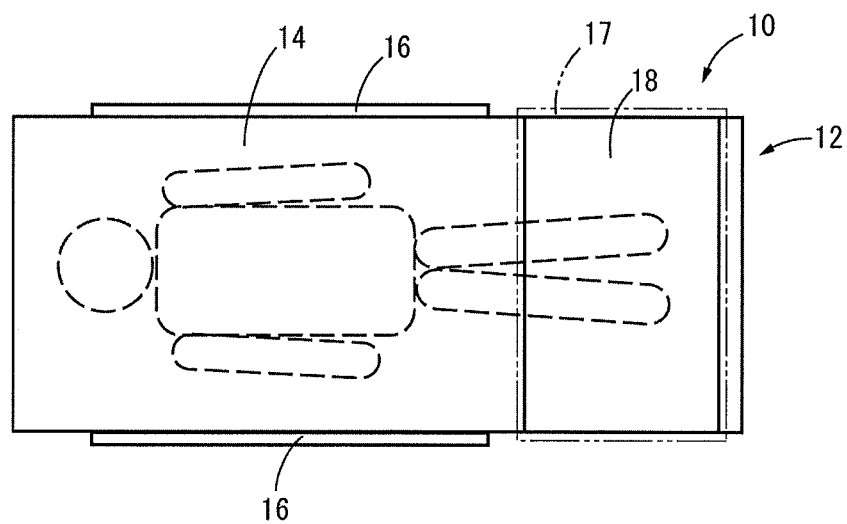
FIG. 2 is a top view of the bed shown in FIG. 1.

First, FIG. 1 and FIG. 2 show a bed 12 equipped with a bed-leaving sensor 10 of a first embodiment of the present invention. The bed 12 is constituted with a base board 14 for supporting a human body being supported by four leg parts 15. With the description hereafter, unless specifically noted, the vertical direction means the lateral direction in FIG. 1 which is the lengthwise direction of the bed 12, and the horizontal direction means the vertical direction in FIG. 2 which is the width direction of the bed 12.

The bed 12 has railings 16, 16 to prevent falling provided at both sides at which the user's torso is positioned. By doing this, with the bed 12, it is possible to leave the bed from a foot side region 17 at which the railings 16, 16 are not provided, and when the user gets down from the bed 12, he leaves the bed from the foot side region 17. In this way, with this embodiment, the bed-leaving possibility region for which it is possible for the user to get down from the bed 12 is set to be only the foot side region 17, and the bed-leaving expectation region assumed to be the sitting position when the user is leaving the bed is set to the foot side region 17.

A pressure sensor 18 is arranged on the base board 14 of the bed 12. The pressure sensor 18 is made to be a size that corresponds to the foot side region 17, and is arranged only on the foot side region 17. Then, the feet of the user on the bed 12 are made to be placed on the pressure sensor 18.

Figure 3:
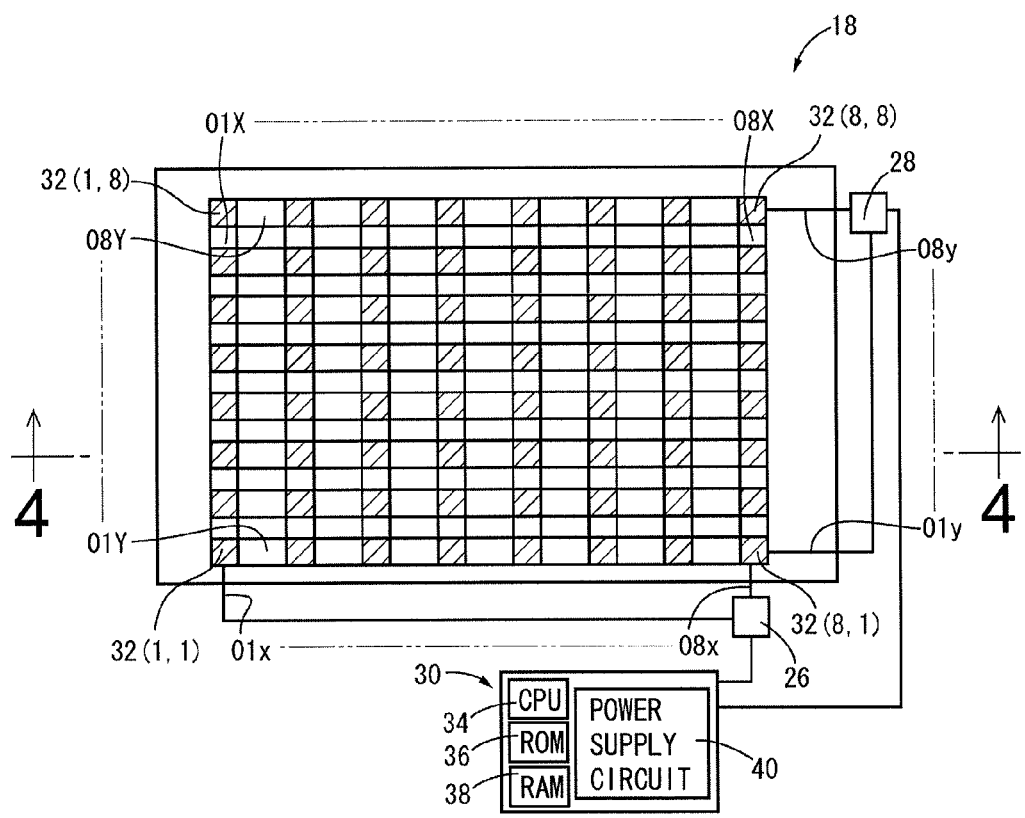
FIG. 3 is a top view of a pressure sensor provided on the bed shown in FIG. 1.
Figure 4:
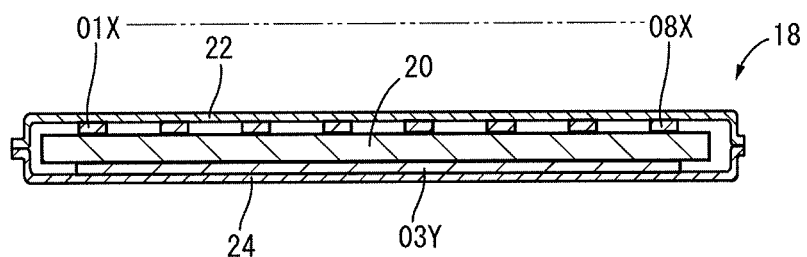
FIG. 4 is a cross section view taken along line 4-4 of FIG. 3.

FIG. 3 and FIG. 4 schematically show the pressure sensor 18. In FIG. 3, to make it easier to understand, a dielectric layer 20 and front side base material 22 described later are illustrated as see-through, and pressure detectors 32 are shown with diagonal lines applied. The pressure sensor 18 is equipped with the dielectric layer 20, front side electrodes 01X to 08X, back side electrodes 01Y to 08Y, front side wiring 01x to 08x, back side wiring 01y to 08y, front side base material 22, back side base material 24, front side wiring connector 26, and back side wiring connector 28, and the front side wiring connector 26 and the back side wiring connector 28 are electrically connected to a data processing device 30. The front side wiring 01x to 08x, the back side wiring 01y to 08y, the front side wiring connector 26, and the back side wiring connector 28 are all arranged within the pressure sensor 18, but in FIG. 3, to make visibility easier, they are shown schematically outside the pressure sensor 18.

The dielectric layer 20 is made of urethane foam as an elastomer, exhibits a sheet shape in a rectangular plate shape, and is elastically deformable. The dielectric layer 20 is of a size that covers the foot side region 17 of the bed 12.

The front side base material 22 is made of rubber, and exhibits a rectangular plate shape. The front side base material 22 is laminated above (front side) the dielectric layer 20. The back side base material 24 is made of rubber, and exhibits a rectangular plate shape. The back side base material 24 is laminated below (back side) the dielectric layer 20.

As shown in FIG. 4, the outer edge of the front side base material 22 and the outer edge of the back side base material 24 are joined, and the front side base material 22 and the back side base material 24 are adhered together in bag form. The dielectric layer 20 is housed inside that bag. The top surface four corners of the dielectric layer 20 are adhered in spot form on the bottom surface four corners of the front side base material 22. Also, the bottom surface four corners of the dielectric layer 20 are adhered in spot form on the top surface four corners of the back side base material 24. In this way, the dielectric layer 20 is aligned so as not to have wrinkles occur during use on the front side base material 22 and the back side base material 24. However, the dielectric layer 20 is elastically deformable in the horizontal direction (front-back and left-right directions) in relation to the front side base material 22 and the back side base material 24 in a state with the four corners adhered.

A total of eight front side electrodes 01X to 08X are arranged on the top surface of the dielectric layer 20. The front side electrodes 01X to 08X are each formed including acrylic rubber and conductive carbon black. The front side electrodes 01X to 08X each exhibit a band shape and are formed so as to be able to expand and contract flexibly. The front side electrodes 01X to 08X each extend in the vertical direction (vertical direction in FIG. 3). The front side electrodes 01X to 08X are separated apart by a designated gap in the horizontal direction (lateral direction in FIG. 3), and are arranged to be roughly parallel to each other.

A total of eight front side wiring 01*x* to 08*x* are arranged on the top surface of the dielectric layer 20. The front side wiring 01*x* to 08*x* are each formed including acrylic rubber and silver powder. The front side wiring 01*x* to 08*x* each exhibit a linear shape. The front side wiring connector 26 is arranged at the corner part of the front side base material 22 and the back side base material 24. The front side wiring 01*x* to 08*x* each connect the front side electrodes 01X to 08X end parts with the front side wiring connector 26.

A total of 8 back side electrodes 01Y to 08Y are arranged on the bottom surface of the dielectric layer 20. The back side electrodes 01Y to 08Y are each formed including acrylic rubber and conductive carbon black. Each of the back side electrodes 01Y to 08Y exhibits a band shape, and are formed to be able to expand and contract flexibly. The back side electrodes 01Y to 08Y each extend horizontally (lateral direction in FIG. 3). The back side electrodes 01Y to 08Y are separated apart by a designated gap in the vertical direction (vertical direction in FIG. 3), and are arranged to be mutually roughly parallel. In this way, the front side electrodes 01X to 08X and the back side electrodes 01Y to 08Y are arranged in a mutually orthogonal matrix form when seen from above or from below.

A total of 8 back side wiring 01*y* to 08*y* are arranged on the bottom surface of the dielectric layer 20. The back side wiring 01*y* to 08*y* are each formed including acrylic rubber and silver powder. The back side wiring 01*y* to 08*y* each exhibit a linear form. The back side wiring connector 28 is arranged at the corner part of the front side base material 22 and the back side base material 24. The back side wiring 01*y* to 08*y* each connect the back side electrode 01Y to 08Y end parts with the back side wiring connector 28.

As shown by the squares to which diagonal lines are applied in FIG. 3, the plurality of pressure detectors 32 that the pressure sensor 18 is equipped with are arranged on the parts for which the front side electrodes 01X to 08X and the back side electrodes 01Y to 08Y intersect in the vertical direction (overlapping parts), and are arranged roughly equally vertically and horizontally across roughly the entire surface of the dielectric layer 20. The pressure detectors 32 are each equipped with a portion of the front side electrodes 01X to 08X, a portion of the back side electrodes 01Y to 08Y, and a portion of the dielectric layer 20. A total of 64 (=8×8) pressure detectors 32 are arranged. With the bed-leaving detection method described later which is executed with the bed-leaving sensor 10, each pressure detector 32, using the front side electrodes 01X to 08X as the x coordinate values and the back side electrodes 01Y to 08Y as the y coordinate values, are recognized as the pressure detectors 32 (x, y). For example, the pressure detector 32 positioned at the lower left corner in FIG. 3 that is arranged at the intersecting part of the front side electrode 01X and the back side electrode 01Y is recognized as pressure detector 32 (1, 1), and the pressure detector 32 positioned at the upper right corner in FIG. 3 that is arranged at the intersecting part of the front side electrode 08X and the back side electrode 08Y is recognized as pressure detector 32 (8, 8).

As shown in FIG. 3, the data processing device 30 is equipped with a CPU (Central Processing Unit) 34, a ROM (Read Only Memory) 36, a RAM (Random Access Memory) 38, and a power supply circuit 40. Stored in the ROM 36 are a detection program shown in FIG. 8 based on the bed-leaving detection method described later, a map indicating the correspondence between the electrostatic capacity of the capacitor constituted by the pressure detectors 32 and the body pressure (load). In the RAM 38, temporarily stored are the calculation values of the detection program, or the output values of the electrostatic capacitance of the pressure detectors 32 input from the front side wiring connector 26 and the back side wiring connector 28. Also, the power supply circuit 40 applies in scanning sequence the periodic square wave voltage to the pressure detectors 32. Then, from the electrostatic capacitance of the pressure detectors 32 stored in the ROM 36, based on the map stored in the ROM 36, the CPU 34 is made to detect body pressure acting on the pressure detectors 32.

As shown in FIG. 1 and FIG. 2, the pressure sensor 18 constituted in this way is overlapped on the foot side region 17 separated from the railings 16, 16 on the base board 14 of the bed 12. Then, when the user lies down on the pressure sensor 18, the body load (body pressure) based on gravity acting on the user is applied to the plurality of pressure detectors 32 of the pressure sensor 18.

Figure 5:
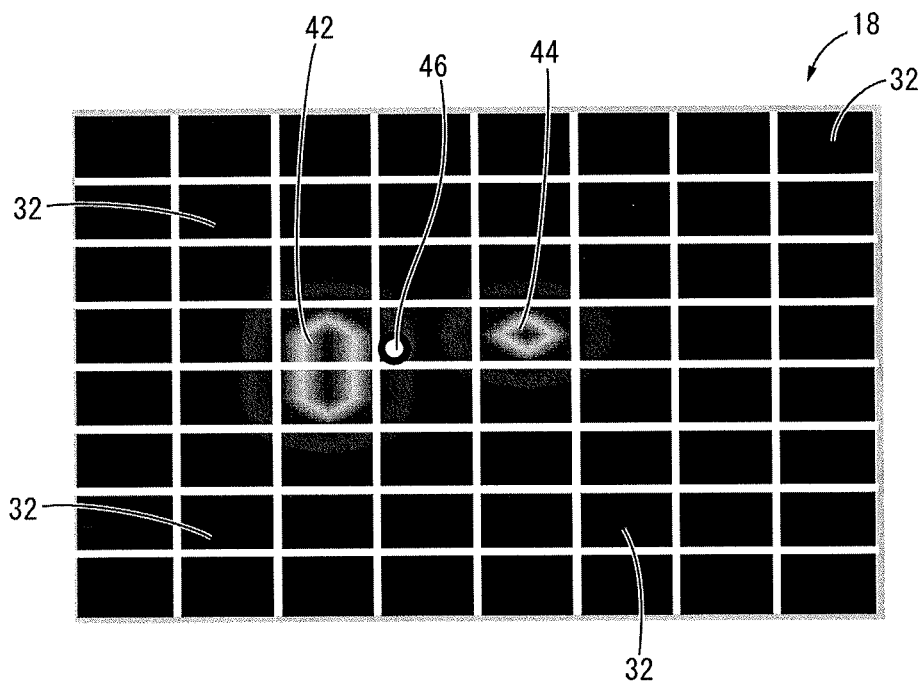
FIG. 5 is an explanatory drawing showing the pressure distribution of the feet during bed-leaving behavior.
Figure 6:
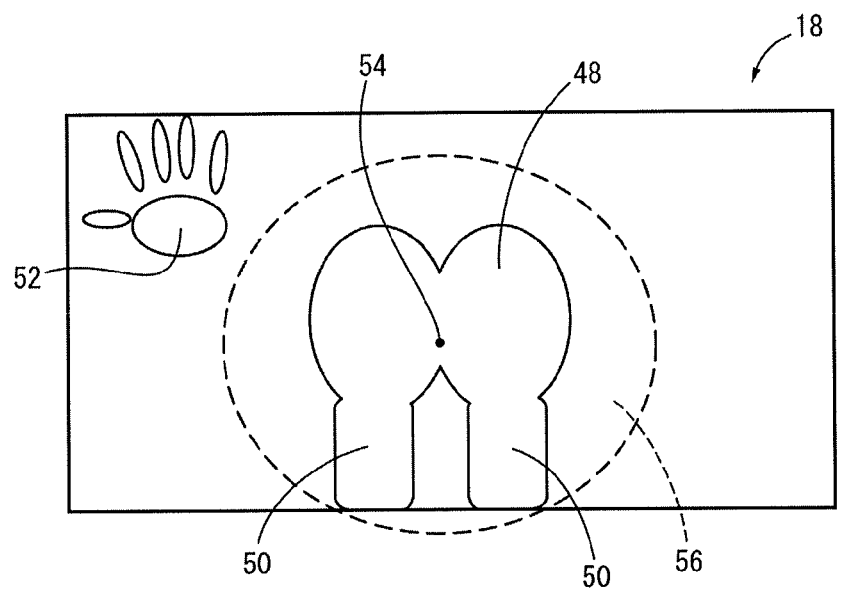
FIG. 6 is an explanatory diagram showing the contact surface of a human body on the pressure sensor when in the sitting position.
Figure 7:
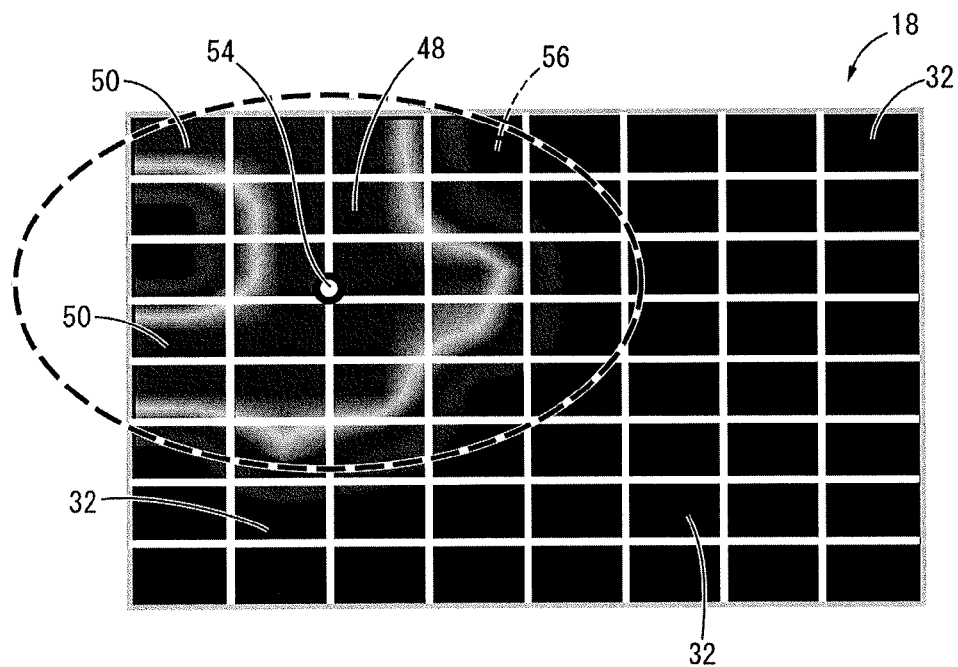
FIG. 7 is an explanatory drawing showing the pressure distribution of the sitting position during bed-leaving behavior.

Next, we will describe in advance a summary of the first embodiment of the present invention as the bed-leaving detection method executed with this kind of data processing device 30 of the bed-leaving sensor 10 while referring to FIG. 5 through 7. FIG. 5 shows the actual pressure distribution on the pressure sensor 18 when pressure is added to the feet when the user is attempting to leave the bed. With this embodiment, the entire surface of the pressure sensor 18 is a foot pressure detection region that detects the movement of the user's feet. Then, the region with the light color in the drawing is the region for which pressure is detected, with code number 42 indicating a right foot of the user and code number 44 indicating a left foot of the user. Respectively in each of these right foot 42 and left foot 44 regions, the pressure increases as the center is approached. The white point of the code number 46 in the drawing is a gravity center of the region combining the right foot 42 and the left foot 44. During bed-leaving behavior linked to bed-leaving, when the user tries to get up, since force is placed on both feet, the pressure value detected with the right foot 42 and the left foot 44 is greater than during normal turning over in one's sleep or the like. Also, with this embodiment, when this kind of pressure distribution is detected across a designated time, it is determined that the feet have moved on the pressure sensor 18, and this is detected as bed-leaving behavior.

Also, FIG. 6 schematically shows the contact surface of the human body on the pressure sensor 18 when in a sitting position, and FIG. 7 shows the actual pressure distribution on the pressure sensor 18 when in a sitting position. With this embodiment, the entire surface of the pressure sensor 18 is a sitting position determination region for determining the sitting position of the user. In the drawing, code number 48 indicates buttocks of the user, and code number 50 indicates femurs of the user. Code number 52 in FIG. 6 indicates a right hand of the user. Also, in FIG. 7, the light colored region is the region for which pressure is detected, and the pressure becomes larger as it approaches a pressure sensing center 54. Then, with this embodiment, even when the user sitting position is detected in the pressure sensor 18 arranged in the foot side region 17 as the bed-leaving expectation region, this is detected as bed-leaving behavior.

Figure 8:
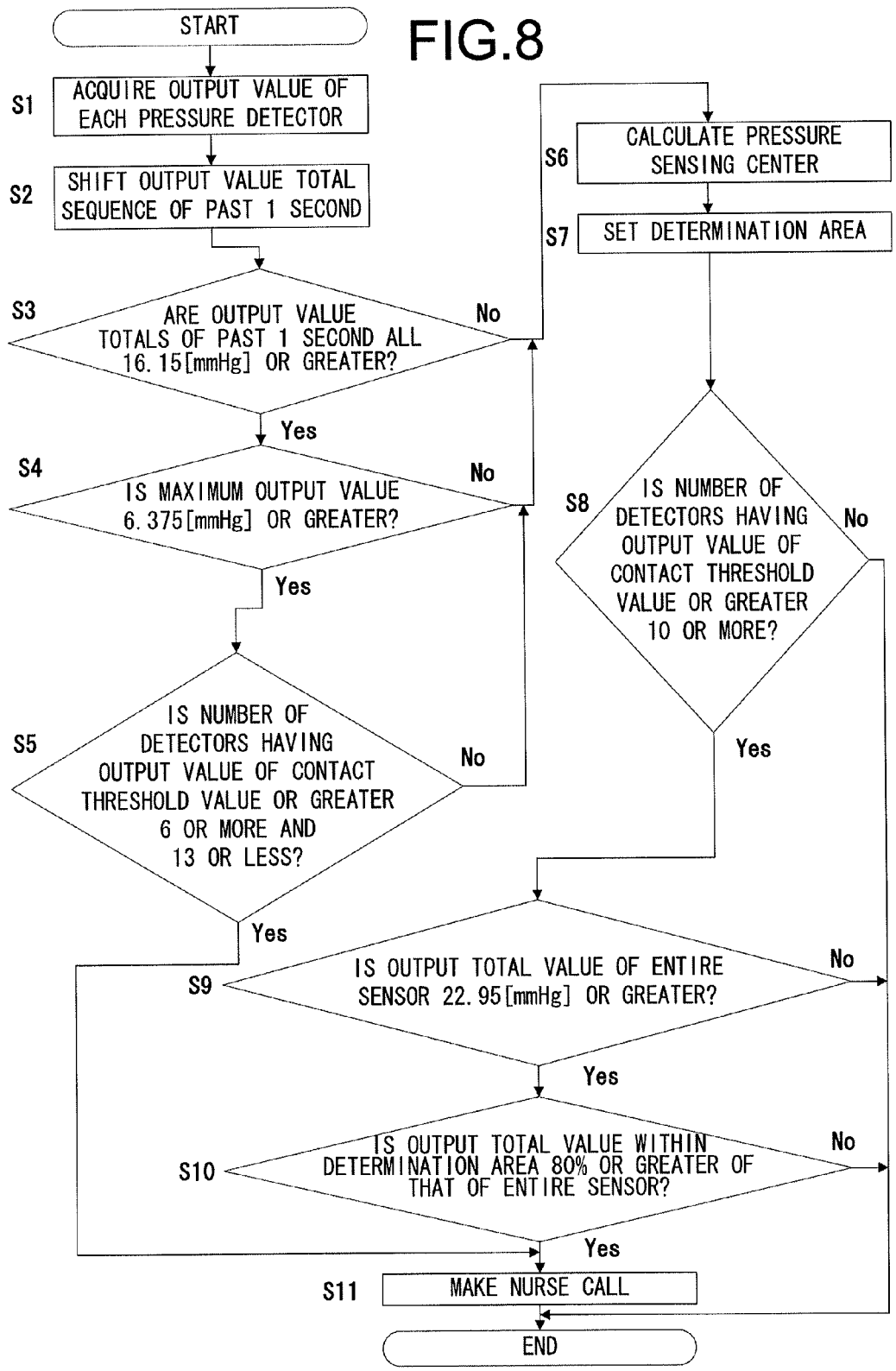
FIG. 8 is a flow chart showing a bed-leaving detection method of a first embodiment of the present invention.

FIG. 8 shows the processing contents executed by the CPU 34 of the data processing device 30. This process is repeatedly executed every designated interval of 0.05 seconds to 1 second, for example. First, at S1, the CPU 34 acquires the output values of all the pressure detectors 32 of the pressure sensor 18.

Next, at S2, the CPU 34 shifts the output value total sequence stored in the RAM 38. The output value total sequence is a sequence for which the total of the output values of the pressure detectors 32 for the past one second can be stored. At S2, the CPU 34 shifts the output value total sequence of the past one second, and stores the total of the output values detected at S1 in the current (most recent) position of the output value total sequence.

Next, at S3, the CPU 34 references the value of the output value total sequence, and determines whether or not the output value totals of the past 1 second are all the designated threshold value (with this embodiment, 16.15 mmHg) or greater. That threshold value can be found and set using the actual measurement or the like of the output value total for which it is possible to determine it is applied from the foot of the user during bed-leaving behavior. When the output value total of the past 1 second is the threshold value or greater (S3=Yes), the CPU 34 executes the processing of S4 and thereafter. Meanwhile, when it is not the threshold value or greater (S3=No), this is regarded as not having foot movement, and the processing of S6 and thereafter is executed.

Subsequently, at S4, the CPU 34 determines whether or not the maximum output value among all the pressure detectors 32 of the pressure sensor 18 is a preset threshold value (with this embodiment, 6.375 mmHg) or greater. That threshold value can also be found and set using the actual measurement or the like of the maximum output value for which it is possible to determine it is applied from the foot of the user during bed-leaving behavior. When the maximum output value is 6.375 mmHg or greater (S4=Yes), the CPU 34 executes the processing of S5 and thereafter. When the maximum output value is not 6.375 mmHg or greater (S4=No), this is regarded as not having foot movement, and the processing of S6 and thereafter is executed.

Furthermore, at S5, the CPU 34 determines whether or not the breadth of the region for which pressure of a contact threshold value or greater is detected at the pressure sensor 18 is within a designated range, specifically, whether or not the number of pressure detectors 32 for which pressure of the contact threshold value or greater is detected is within a designated range (with this embodiment, 6 or more and 13 or less). The contact threshold value is a value that can be recognized as something having significant contact with the pressure detectors 32, and is a value that can be set freely to distinguish the pressure detectors 32 being used significantly for sitting position determination. For example, with this embodiment, it is set to 1.6 mmHg. Also, for the designated range of the breadth of the region of the contact threshold value or greater, a value correlating to the size of the foot that is found and set using actual measurement or the like. When the number of pressure detectors 32 of the contact threshold value or greater is 6 or more and 13 or less (S5=Yes), the CPU 34 determines that this is bed-leaving behavior for which the foot is moving on the foot side region 17 on which the pressure sensor 18 is arranged, and at S11, makes a nurse call. With the nurse call, for example, through an electric line connected to the data processing device 30, a warning sound is rung or a warning lamp is displayed at a nurse station separated from the room in which the bed 12 is placed, and notification is given to a caregiver in the nurse station that the user is in the process of leaving the bed. After the nurse call (S11) ends, the CPU 34 ends processing.

Meanwhile, when the number of pressure detectors 32 of the contact threshold value or greater is neither 6 or more nor 13 or less (S5=No), the CPU 34 regards this as not having foot movement, and at S6, calculates the pressure sensing center 54 shown in FIG. 6 and FIG. 7, and this is stored in the RAM 38. The pressure sensing center 54 is sufficient as long as it is possible to roughly identify the center part of the region for which pressure is detected with the pressure sensor 18, and with this embodiment, based on the formula below, the gravity center of the plurality of pressure detectors 32 having output values of a preset contact threshold value or greater is made to be calculated as the coordinate values ($C_{px}$, $C_{py}$) of the pressure detectors 32. With the formula below, when any of the pressure detectors 32 (x, y) is i, the output value of that pressure detector 32 is expressed as $p_i$, the x coordinate value as $x_i$, and the y coordinate value as $y_i$. Also, the total count of all the pressure detectors 32 (x, y) is expressed as N, and the contact threshold value as t.

$$Cpx = \frac{\sum_{i=1}^{N}(Pi \times Xi)}{\sum_{i=1}^{N} Pi}, \quad Cpy = \frac{\sum_{i=1}^{N}(Pi \times Yi)}{\sum_{i=1}^{N} Pi} \quad \text{[Formula 1]}$$

Note that when $Pi < t$, $Pi = 0$

As the pressure sensing center 54, it is also possible to use the area center of the region for which pressure of a contact threshold value or greater is detected with the pressure sensor 18. The area center can be calculated based on the formula below for example as the coordinate value ($C_{ax}$, $C_{ay}$) of the pressure detectors 32. With the formula below, the number of pressure detectors 32 (x, y) having an output value of the contact threshold value or greater is expressed as n. Working in this way, the calculation process is simplified, and it is possible to perform determination more rapidly.

$$Cax = \frac{\sum_{i=1}^{n} Xi}{n}, \quad Cay = \frac{\sum_{i=1}^{n} Yi}{n} \quad \text{[Formula 2]}$$

Next, at S7, the CPU 34 sets a designated radius, circular determination area 56 with the pressure sensing center 54 shown in FIGS. 6 and 7 as the center. The radius of the determination area 56 can be set freely considering the overall size of the pressure sensor 18, the arrangement pitch of the pressure detectors 32 or the like, but with this embodiment, the coordinate value of the pressure detector 32 is 3.

Subsequently, at S8, the CPU 34 determines whether or not the breadth of the region having an output value of a preset contact threshold value or greater is a designated value or greater, specifically, whether or not the number of pressure detectors 32 having an output value of a contact threshold value or greater is 10 or more, and when it is 10 or more (S8=Yes), executes the processing of S9 and thereafter, and when it is not 10 or more (S8=No), ends processing.

Next, at S9, the CPU 34 determines whether or not the total of the output values of the pressure detectors 32 of the entire pressure sensor 18 is a designated threshold value (with this embodiment, 22.95 mmHg) or greater. When the total of the output values is the threshold value or greater (S9=Yes), the process of S10 and thereafter is executed, and when the total of the output values is not the threshold value or greater (S9=No), the process ends.

Furthermore, at S10, the CPU 34 determines whether or not the ratio of the output total value of the pressure detectors 32 positioned within the determination area 56 occupying the output total value of the pressure detectors 32 of the entire pressure sensor 18 is a designated threshold value (with this embodiment, 80%) or greater. When it is the threshold value or greater (S10=Yes), the CPU 34 determines that bed-leaving behavior which is the user in a sitting position in the foot side region 17 is being performed, and at S11, a nurse call is performed, and processing ends. On the other hand, if not the threshold value or greater (S10=No), this is regarded as not having the user be in a sitting position on the foot side region 17, so it is not bed-leaving behavior, and the processing ends without performing a nurse call.

In this way, with this embodiment, the foot movement detection step is constituted including S3 to S5, and the foot movement detection member is constituted including the data processing device 30, and S3 to S5. Also, the sitting position detection step is constituted including S8 to S10, and the sitting position detection member is constituted including the data processing device 30, and S8 to S10. Also, the bed-leaving behavior detection step is constituted including S3 to S5 and S8 to S10, and the bed-leaving behavior detection member is constituted including the data processing device 30, S3 to S5, and S8 to S10. Also, the notification member is constituted including the data processing device 30 and S11.

With this embodiment, when the user takes a sitting position posture in the foot side region 17 for which bed-leaving is possible outside the railings 16, 16 of the bed 12, this is detected as bed-leaving behavior connected to bed-leaving, and a nurse call is performed. By doing this, it is possible to perform a nurse call before complete bed-leaving by the user from the bed 12. Furthermore, since bed-leaving behavior is determined when the sitting position is detected with the foot side region 17, it is possible to distinguish from a simple sitting position, and possible to determine bed-leaving behavior with better precision. As a result, it is possible to decrease false alarms, and possible to avoid having nurse calls performed frequently. In particular, with the pressure sensor 18, the determination area 56 is set in the periphery of the pressure sensing center 54 of the region for which pressure was detected, and by detecting the user sitting position based on the size of the determination area 56, the ratio occupied in the pressure sensor 18 overall or the like, it is possible to detect the sitting position with good precision without depending on a fixed direction of the device itself.

Also, when foot movement is detected with the foot side region 17, this is regarded as bed-leaving behavior occurring and a nurse call is performed. By doing this, it is possible to detect bed-leaving behavior at the stage at which an attempt is made to move the buttocks to the foot side region 17 before the user buttocks reach the foot side region 17, and it is possible to detect bed-leaving at an earlier stage. Also, by determining the movement of the feet as bed-leaving behavior with the maximum value of the pressure applied to the pressure sensor 18 from the user feet or pressure of a designated level or greater continuing over a designated time (with this embodiment, 1 second) as a condition, it is possible to distinguish between foot movement of simple turning over or the like from foot movement as bed-leaving behavior, and possible to detect bed-leaving behavior with good precision.

Furthermore, with this embodiment, the pressure sensor 18 is arranged only in the foot side region 17 as the bed-leaving possibility region. By doing this, it is possible to make the pressure sensor 18 more compact, and possible to ensure good sleep comfort for the user. Also, by arranging the pressure sensor 18 at the foot side region 17 which is the area that does not have railings 16, 16 of the bed 12, it is possible to reliably have the sitting position by the user when leaving the bed on the pressure sensor 18, and possible to reliably detect the sitting position of the user when leaving the bed.

Above, we gave a detailed description of a plurality of embodiments of the bed-leaving sensor and the bed-leaving detection method of the present invention, but the present invention is not limited to these specific notations. For example, the bed-leaving expectation region, the sitting position determination region or the foot pressure detection region for which the sitting position or the foot movement is detected can be set freely considering the bed arrangement environment, the assumed movement at the time the user leaves the bed or the like, and in a case such as when the bed is arranged along a building wall, it is also possible to set the bed-leaving expectation region or the sitting position determination region from the head side of the outer peripheral part on the opposite side to the wall toward the foot side, or the like. Also, with the pressure sensor, it is possible to arrange this on the entire surface of the bed, and possible to set the bed-leaving expectation region, the sitting position determination region, and the foot pressure detection region in a portion of the pressure sensor. For example, while arranging the pressure sensor on the entire surface of the bed, it is possible to set the bed-leaving expectation region, the sitting position determination region, and the foot pressure detection region only at the foot side region with the pressure sensor. Furthermore, the sitting position determination region for detecting the sitting position and the foot pressure detection region for detecting the foot movement can be set at mutually different regions, and for example in a case when the pressure sensor is arranged on the entire surface of the bed, while the foot pressure detection region is set in the foot side region of the bed, the sitting position determination region can be set to the outer circumference end part extending to the foot side from the head side of the bed or the like.

Also, the specific values of the threshold values or the like shown with each of the embodiments can be set as appropriate considering the physique of the user, the size of the bed and the pressure sensor, the number of pressure detectors provided in the pressure sensor and the like, and it is not limited to the specific numerical values in the embodiments. Therefore, for example, the contact threshold value can be made to be changeable for each user according to the user's weight or the like.

What is claimed is:

1. A bed-leaving sensor for detecting bed-leaving by a user on a bed, comprising:
 a sitting position detection member that detects a sitting position of the user based on a detection value of a pressure sensor arranged on the bed;
 a foot movement detection member for detecting foot movement of the user based on the detection value of the pressure sensor; and
 a bed-leaving behavior detection member that detects bed-leaving behavior of the user with the sitting position or the foot movement being detected within a preset bed-leaving expectation region as a condition,
 wherein the sitting position detection member sets a determination area in a periphery of a pressure sensing center of a region in which pressure of a given contact threshold value or greater is detected within a preset sitting position determination region on the pressure sensor provided on the bed-leaving, expectation region, and the sitting position is detected based on fulfilling all the following requirements:
  a ratio of a total pressure detected within the determination area occupying a total pressure detected within the sitting position determination region is a designated threshold value or greater;
  a breadth of the region in which the pressure of the contact threshold value or greater is detected within the sitting position determination region is a designated value or greater; and
  the total pressure detected within the sitting position determination region is a designated threshold value or greater, and
wherein the foot movement detection member detects the foot movement based on fulfilling all the following requirements:
  a breadth of a region in which pressure of a given contact threshold value or greater has been detected within a preset foot pressure detection region on the pressure sensor provided on the bed-leaving expectation region is within a designated range;
  a total pressure detected within the foot pressure detection region across a given time is a designated threshold value or greater; and
  a maximum pressure value detected within the foot pressure detection region is a preset threshold value or greater.

2. The bed-leaving sensor according to claim 1, wherein the bed-leaving expectation region is set to be a foot side region on the bed.

3. The bed-leaving sensor according to claim 1, wherein the pressure sensor is arranged only at a bed-leaving possibility region on the bed.

4. The bed-leaving sensor according to claim 1, wherein the pressure sensing center is a center of gravity of the region in which the pressure of the contact threshold value or greater is detected with the pressure sensor.

5. The bed-leaving sensor according to claim 1, wherein the pressure sensing center is an area center of the region in which the pressure of the contact threshold value or greater is detected with the pressure sensor.

6. The bed-leaving sensor according to claim 1, further comprising a notification member for notifying that the bed-leaving behavior of the user has been detected.

7. A bed-leaving detection method for detecting bed-leaving by a user on a bed, comprising:

a sitting position detection step for detecting a sitting position of the user based on a detection value of a pressure sensor arranged on the bed;
a foot movement detection step for detecting foot movement of the user based on the detection value of the pressure sensor; and
a bed-leaving behavior detection step for detecting bed-leaving behavior of the user with the sitting position or the foot movement being detected within a preset bed-leaving expectation region as a condition,
wherein with the sitting position detection step, a determination area is set in a periphery of a pressure sensing center of a region in which pressure of a given contact threshold value or greater is detected within a preset sitting position determination region on the pressure sensor provided on the bed-leaving expectation region, and the setting position is detected based on fulfilling all the following requirements:
  a ratio of a total pressure detected within the determination area occupying a total pressure detected within the sitting position determination region is a designated threshold value or greater;
  a breadth of the region in which the pressure of the contact threshold value or greater is detected within the sitting position determination region is a designated value or greater; and
  the total pressure detected within the sitting position determination region is a designated threshold value or greater, and
wherein the foot movement detection step detects the foot movement based on fulfilling all the following requirements:
  a breadth of a region in which pressure of a given contact threshold value or greater is detected within a preset foot pressure detection region on the pressure sensor provided on the bed-leaving expectation region is within a designated range;
  a total pressure detected within the foot pressure detection region across a given time is a designated threshold value or greater, and
  a maximum pressure value detected within the foot pressure detection region is a preset threshold value or greater.

8. The bed-leaving detection method according to claim 7, wherein a foot side region on the bed is set as the bed-leaving expectation region.

* * * * *